United States Patent [19]
Lewis

[11] Patent Number: 5,368,595
[45] Date of Patent: Nov. 29, 1994

[54] IMPLANT ASSIST APPARATUS

[75] Inventor: Royce Lewis, Lubbock, Tex.

[73] Assignee: United States Surgical Corporation, Norwalk, Conn.

[21] Appl. No.: 578,552

[22] Filed: Sep. 6, 1990

[51] Int. Cl.$^5$ .................. A61B 17/56; A61L 17/00
[52] U.S. Cl. ........................................ 606/72; 606/228
[58] Field of Search .................. 606/72, 73, 77, 227, 606/222, 238, 224, 230, 233, 232, 74, 75, 76, 220, 226; 411/340, 508, 509, 510, 511, 904

[56] References Cited

U.S. PATENT DOCUMENTS

| | | |
|---|---|---|
| 353,040 | 11/1886 | Strain . |
| 2,570,465 | 10/1951 | Lundholm .................. 606/73 |
| 2,833,284 | 5/1958 | Springer . |
| 3,035,583 | 5/1962 | Hirsch et al. . |
| 3,125,095 | 3/1964 | Kaufman et al. . |
| 3,212,502 | 10/1965 | Meyers .................. 606/224 |
| 3,385,300 | 5/1968 | Holter .................. 604/275 |
| 3,875,946 | 4/1975 | Duncan .................. 606/227 |
| 4,235,238 | 11/1980 | Ogiu et al. .................. 606/145 |
| 4,265,246 | 5/1981 | Barry . |
| 4,345,601 | 8/1982 | Fukuda .................. 606/147 |
| 4,364,391 | 12/1982 | Toye .................. 128/207.15 |
| 4,392,495 | 7/1983 | Bayers .................. 606/148 |
| 4,471,778 | 9/1984 | Toye .................. 604/160 |
| 4,510,934 | 4/1985 | Batra .................. 606/231 |
| 4,537,185 | 8/1985 | Stednitz .................. 606/73 |
| 4,583,540 | 4/1986 | Malmin .................. 606/187 |
| 4,625,717 | 12/1986 | Covitz .................. 606/74 |
| 4,632,100 | 12/1986 | Somers .................. 606/73 |
| 4,643,178 | 2/1987 | Nastari et al. .................. 606/74 |
| 4,683,885 | 8/1987 | Hutterer et al. . |
| 4,778,468 | 10/1988 | Hunt et al. . |
| 4,784,139 | 11/1988 | Demos .................. 606/148 |
| 4,792,336 | 12/1988 | Hlavacek .................. 606/72 |
| 4,799,483 | 1/1989 | Kraff . |
| 4,803,984 | 2/1989 | Narayanan et al. .................. 606/148 |
| 4,819,640 | 4/1989 | Narayanan et al. .................. 606/148 |
| 4,899,743 | 2/1990 | Nicholson et al. . |
| 4,901,721 | 2/1990 | Hakki . |
| 4,927,421 | 5/1990 | Goble .................. 606/73 |
| 4,932,962 | 6/1990 | Yoon et al. . |
| 4,950,270 | 8/1990 | Bowman .................. 606/72 |
| 4,968,315 | 11/1990 | Gatturna . |
| 4,989,764 | 2/1991 | Hoffman et al. . |
| 5,037,422 | 8/1991 | Hayhurst .................. 606/72 |
| 5,041,129 | 8/1991 | Hayhurst et al. .................. 606/233 |
| 5,089,012 | 2/1992 | Prou . |
| 5,098,435 | 3/1992 | Stednitz et al. . |

FOREIGN PATENT DOCUMENTS

| | | |
|---|---|---|
| 0478949 | 4/1992 | European Pat. Off. . |
| 1478221 | 3/1967 | France . |
| 2422386 | 11/1979 | France . |

*Primary Examiner*—Robert A. Hafer
*Assistant Examiner*—Michael Brown

[57] ABSTRACT

An implant assist apparatus is disclosed for implanting material such as a suture in tissue to reapproximate or reinforce the tissue. A cannula is provided having a hollow body and an open proximal and distal end. Point means is detachably fixed to the open proximal end of the cannula for penetrating tissue. A method of implanting the material in tissue for reapproximating or reinforcing the tissue with the implant assist apparatus is also disclosed whereby a length of the implant material is attached to a guide wire for partial containment within the cannula. The cannula with detachable point is passed into the tissue at an entry point remote from one side of the defect and out an exit point on the opposite side remote from the defect such that the distal end of the hollow body extends from the entry point and a proximal end extends from the exit point. The detachable point is removed from the cannula and a guide wire with implant material attached is drawn out of the proximal end of the hollow body until the implant material is exposed at both the distal and proximal ends of the hollow body. Thereafter, the cannula is withdrawn from the tissue leaving the implant material in place and the implant material is anchored to reapproximate or reinforce the defect.

29 Claims, 4 Drawing Sheets

IMPLANT ASSIST APPARATUS

BACKGROUND OF THE INVENTION

1. Field of the Invention

The present invention relates to a method and apparatus for effectively joining and/or reinforcing separated soft tissues in humans and animals. More particularly, the invention is directed to a method and apparatus for placement of implants for reapproximating separations in or reinforcing weakened or separated soft tissues normally subject to flexure or strains such as for example, muscles, tendons or ligaments without excessive abrasion.

2. Description of Related Art

Currently, end to end repair of elastic tissue such as muscles, tendons and ligaments, separated either by surgical procedure or injury, involves suturing the ends of the tissue together for a time sufficient to permit normal healing. The ends of the tissue are joined with a wide variety of both absorbable and nonabsorbable suture and implant materials. With nonabsorbable suture materials, the sutures are typically removed within one or two weeks of implantation or left in place.

Conventional curved suture needles, with their small radii, significantly limit the distance over which the suture can be buried. This limitation requires that the sutures be positioned proximal to the severed ends of the tissue. Particularly, in the case of soft elastic tissue such as muscles, tendons or ligaments, conventionally implanted sutures have a tendency to prematurely pull through the joined ends of the tissue when it is flexed or subject to slight strains. When this occurs, the tissue ends separate and healing is arrested necessitating further surgery to repair the damage. One particularly advantageous suture for use in joining ends of soft elastic tissue is a braided suture. Braided sutures are well known in the art and are more supple and workable than conventional monofilament sutures for a given tensile strength. Braided sutures, however, tend to abrade these types of soft tissue as they are implanted. It is desirable to be able to introduce a relatively rough-surfaced braided suture without causing tissue damage because, once in place, this type of suture may provide some frictional resistance to pull-out, keep the two ends of the tissue being reapproximated from pistoning and provide a scaffold for tissue ingrowth as healing progresses thus reinforcing the repair.

It is also common to repair, reinforce or replace tendons and ligaments with prosthetic devices, as for example the anterior cruciate ligament. Prosthetic ligaments such as the Gore-Tex cruciate ligament device are generally implanted through tunnels and anchored at either end. After the tunnels are drilled, it is generally viewed as important to chamfer both the internal and external surfaces to remove sharp edges in an attempt to prevent damage to the prosthesis during placement.

Other common types of procedures involving the reapproximation or reinforcing of tissue ends by implant material include, inter alia, patellar reconstruction, collateral ligament repair, knee repair, rotator cuff, tendon suturing, muscle facia suturing, tendon advancement, reattachment or grafting as well as muscle transfer.

Therefore, it would be highly desirable to have a method and apparatus which permits implant materials of all types to be easily and efficiently positioned in soft or hard tissue over an extended distance remote from ends of the tissue to be joined without excessive abrasion.

Accordingly, it is one object of the present invention to provide apparatus which facilitates placement of implant materials within soft or hard tissue over extended distances beyond the ends of the tissue to be joined.

It is a further object of the present invention to provide an apparatus which protects the soft or hard tissue and the implant material from abrasion during implantation.

It is another object of the present invention to provide a method and apparatus for implanting an implant material within soft or hard tissue over extended distances without excessive abrasion to the tissue or implant material.

These and other highly desirable and unusual results are accomplished by the present invention in a method and apparatus for implanting an implant material over extended distances within soft or hard tissue to reapproximate and/or reinforce separated ends of the tissue and thus resist the tendency to prematurely pull through the ends of the reapproximated or reinforced tissues when subject to flexure or slight strain. The apparatus and method further permit implantation of a wide variety of implant materials such as sutures, including braided sutures, prosthetic devices such as, for example, tapes, ribbons, braided hollow tubes or other elongated structures, in whole or in part, or tissue augmentation devices without excessive abrasion to the tissue or the implant material.

Objects and advantages of the invention are set forth in part herein and in part will be obvious therefrom, or may be learned by practice with the invention, which is realized and attained by means of instrumentalities and combinations pointed out in the appended claims. The invention consists of novel parts, constructions, arrangements, combinations, steps and improvements herein shown and described.

SUMMARY OF THE INVENTION

According to the present invention, a method and apparatus is provided for facilitating the reapproximation and/or reinforcing of separated ends of soft or hard tissue of human and animal bodies by placement of implant materials to promote healing. The apparatus comprises a cannula with a removable point releasably attached to one end. The cannula is dimensioned in length, shape and diameter based upon, inter alia, the type of implant material to be implanted, the length of tissue through which the implant material is to pass and the characteristics including shape, of the tissue. For example, in the repair of small tendons or ligaments, a curved cannula approximately four inches in length and 16 or 18 gage in diameter would permit the implantation of a stay suture wherein the suture would extend through the tissue defect and emerge on either end approximately two inches remote from the defect.

The removable point serves to convert the cannula into a hollow trocar to provide smooth passage of the cannula through the tissue, particularly soft tissue, with minimal damage. Further support and guidance through the tissue may be obtained by providing flutes or grooves longitudinally along the outer body of the cannula adjacent the point.

Once the hollow trocar is in position within the tissue to be approximated or reinforced, the removable point is detached, converting the hollow trocar back into a cannula, open at both ends and ready to receive and guide an implant material. The implant material is threaded through the cannula until it is in position with an end of the implant material extending from either end of the cannula. A guide wire may be fixed to the removable point to aid in threading of the implant material through the cannula. The guide wire is attached proximal the base of the point and extends through the cannula, terminating in a loop which is accessible from the end of the hollow trocar.

Implant material ends may also be preattached to the base of the point so that when the point is removed the implant material is already in place. When the cannula is removed, the implant material is embedded in the midsubstance of the tissue. The number of implant ends attached to the point can vary from one to any multiple desired for a given procedure, with two ends being preferred.

Thereafter, the cannula is withdrawn from the tissue leaving the implant material in place therein to securely approximate and/or reinforce the separated ends of the tissue. Final closure of the edges of the defect may be accomplished by suitable means, e.g., small sutures, if necessary. However, the main implanted suture serves to support and distribute flexure and strain forces applied to the joined tissue to facilitate healing.

BRIEF DESCRIPTION OF THE DRAWINGS

The accompanying drawings, referred to herein and constituting a part hereof, illustrate preferred embodiments of the present invention and, together with the description, serve to explain the principles of the present invention.

DETAILED DESCRIPTION OF THE PREFERRED EMBODIMENTS

Figure 1:
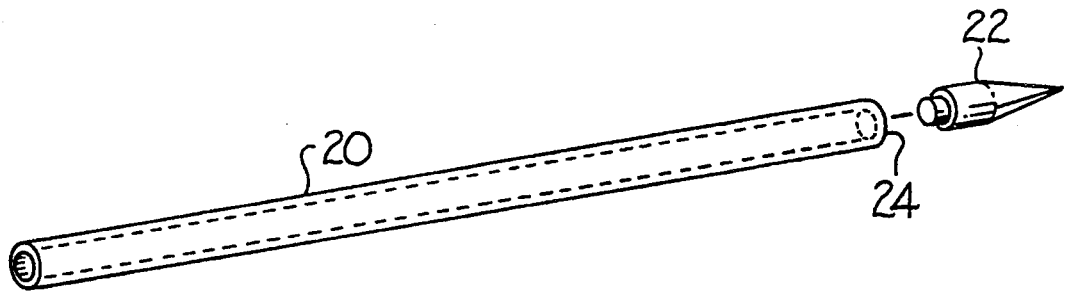
FIG. 1 is a side view of one embodiment of the present invention having a substantially linear cannula with removable trocar point.

FIGS. 1-4 show a variety of preferred embodiments of the apparatus in accordance with the present invention. FIG. 1 represents a substantially linear cannula 20 having a removable point 22 detachably positioned in a proximal end 24 of linear cannula 20. Removable point 22 is press fit with a slight interference into proximal end 24 to facilitate secure attachment and easy removal. One skilled in the art, however, would recognize that any releasable attachment means would be appropriate including, threading, twist on or breakaway lines.

Point 22 is formed in the shape of a trocar to ease entry into soft tissue. Other shapes and configurations are also useful including: conical, both convex and concave; arcuate conical; tapered; reverse cutting; side cutting; and flattened conical with a plurality of sharpened edges. In order to ease entry of the cannula into the tissue, the points are dimensioned at their base to have approximately the same diameter as the cannula to which they are attached.

Cannula 20 is dimensioned based on the particular application and the type of approximating or reinforcing material to be implanted. For example, in hand tendon repair, cannulas of 16 or 18 gage diameter in varying lengths are particularly useful for implanting suture material to join separated ends. For other applications such as larger tendons, muscle, soft tissue or ligament repair, size, shape, length and diameter may be varied as required.

Figure 1A:
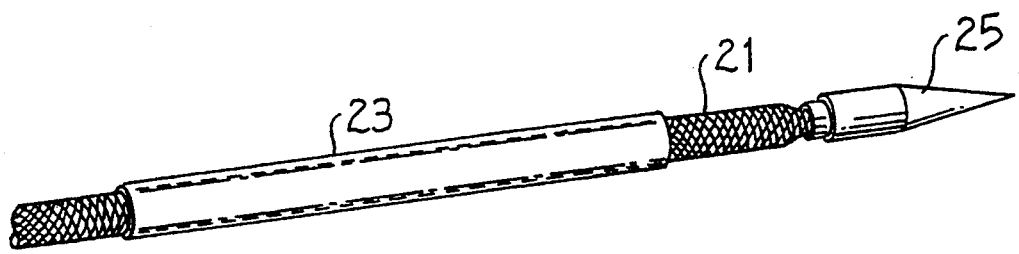
FIG. 1A is an enlarged side view of one embodiment of the present invention for implanting a braided tubular ligament prosthesis using a linear cannula with the prosthesis attached to a removable taper point.

FIG. 1A discloses an alternate embodiment of the present invention for implanting a braided tubular ligament prosthesis 21. A substantially linear cannula 23 encloses a portion of the prosthesis 21, one end of which is fixed directly to removable taper point 25. This point 25 is press fit in a similar manner to that described above with respect to the embodiment of FIG. 1.

Figure 2:
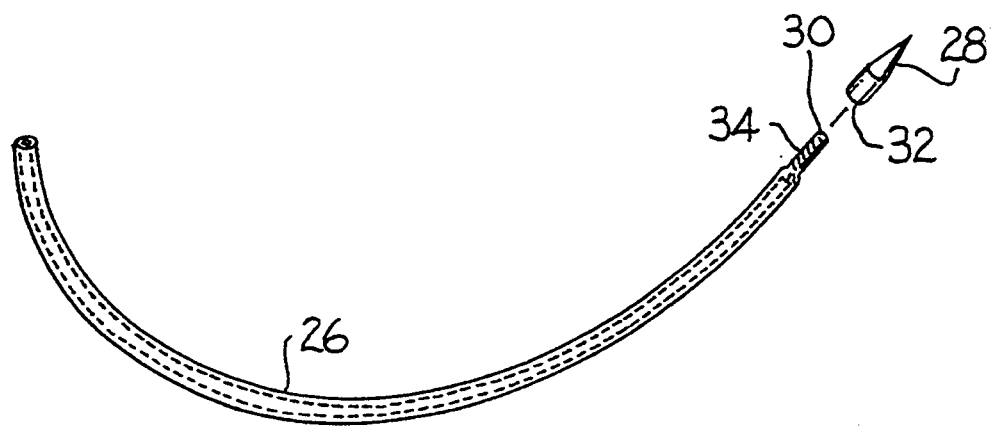
FIG. 2 is a side view of another embodiment of the present invention having an arcuate cannula with removable cut taper point.

FIG. 2 shows a substantially arcuate cannula 26 having a removable point 28 which is releasably attachable to a proximal end 30 of cannula 26. In this embodiment, point 28 is provided with internal threads 32 which are threadably engagable with external threads 34 formed on proximal end 30 of cannula 26. Alternatively, annular rings and grooves could be substituted for threads 32, 34 such that point 28 interfits over cannula 26.

Figure 3:
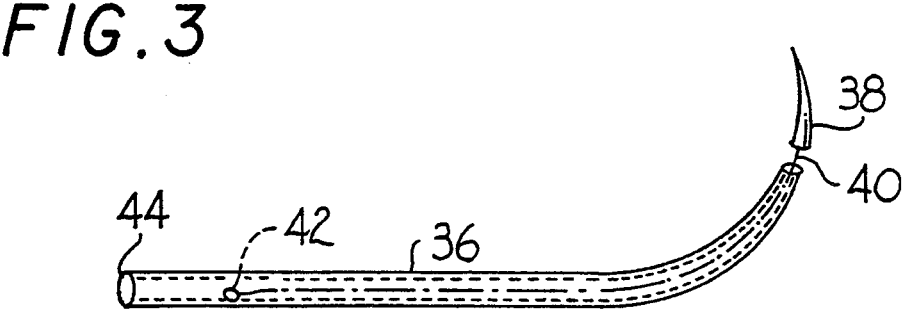
FIG. 3 is a side view of still another embodiment of the present invention having a partially linear and partially arcuate cannula with a removable point having a guide wire attached.

A cannula 36 having a partially linear and partially arcuate shape is shown in FIG. 3. This embodiment of the present invention also includes a removable point 38 which is formed in the shape of an arcuate cone following the curve of cannula 36.

A guide wire 40 is affixed to the base of removable point 38 and extends through cannula 36, terminating in loop 42 at a distal end. This loop 42 may either extend slightly beyond the distal end 44 of cannula 36 (FIG. 3B) or remain within the cannula to facilitate attachment of an implant material (not shown) to be drawn through cannula 36 by guide wire 40.

Figure 3A:
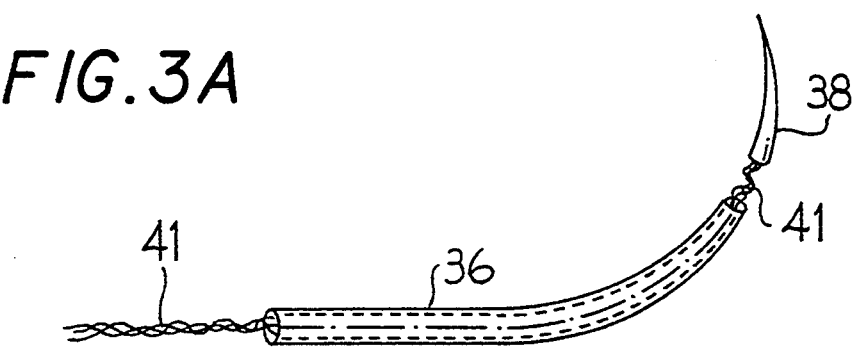
FIG. 3A is a side view of an alternate embodiment of the present invention having the implant material fixed directly to the removable point.
Figure 3B:
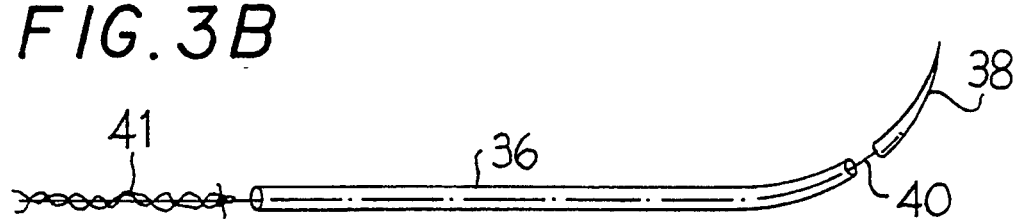
FIG. 3B is a side view of an embodiment of the present invention wherein the guide wire extends through the canula and has the implant material attached to a loop outside the cannula.

Alternatively, an implant material such as, for example, a braided suture 41, may be fixed directly to removable point 38 as shown in FIG. 3A. This configuration would serve to pull the braided suture 41 directly into position simply by removing point 38.

Figure 4:
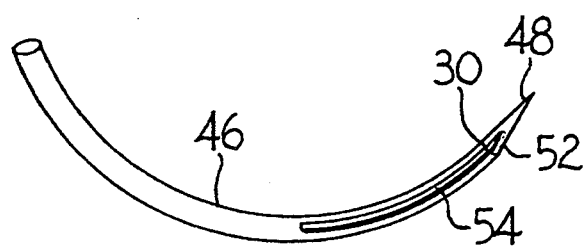
FIG. 4 is a side view of another embodiment of the present invention having an arcuate fluted cannula with a removable point and guide wire.

Another embodiment of the present invention is shown in FIG. 4 wherein a cannula 46 is formed with a breakaway point 48. In this embodiment the entire assembly (cannula 46 and breakaway point 48) is formed as a single unit with a preformed breakaway line 50 to enable point 48 to be broken off after positioning, leaving cannula 46 in place. This assembly can be formed using known techniques such as, for example, extrusion, molding, etc. Appropriate materials include, stiff or reinforced plastics, aluminum, stainless steel, etc.

The breakaway point 48 of this embodiment is in the shape of a flattened cone with sharp edges 52. Further, flutes 54 are provided longitudinally along cannula 46 to aid and guide the assembly through the tissue.

Figure 5:
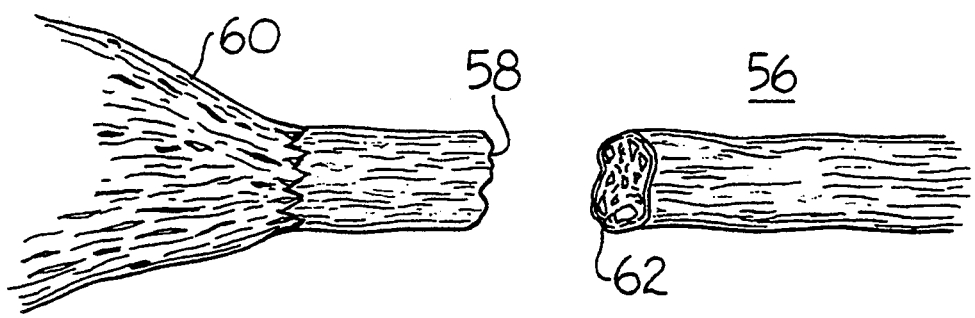
FIGS. 5-10 are perspective views of a tendon repair using apparatus in accordance with the present invention to implant a braided stay suture.

FIGS. 5-10 illustrate the use of one embodiment of the present implant assist apparatus to repair a defect in a tendon using a braided type stay suture. FIG. 5 shows the tendon, generally 56, separated into a first end 58 proximate muscle tissue 60 and a second end 62 proximate the bone (not shown).

Figure 6:
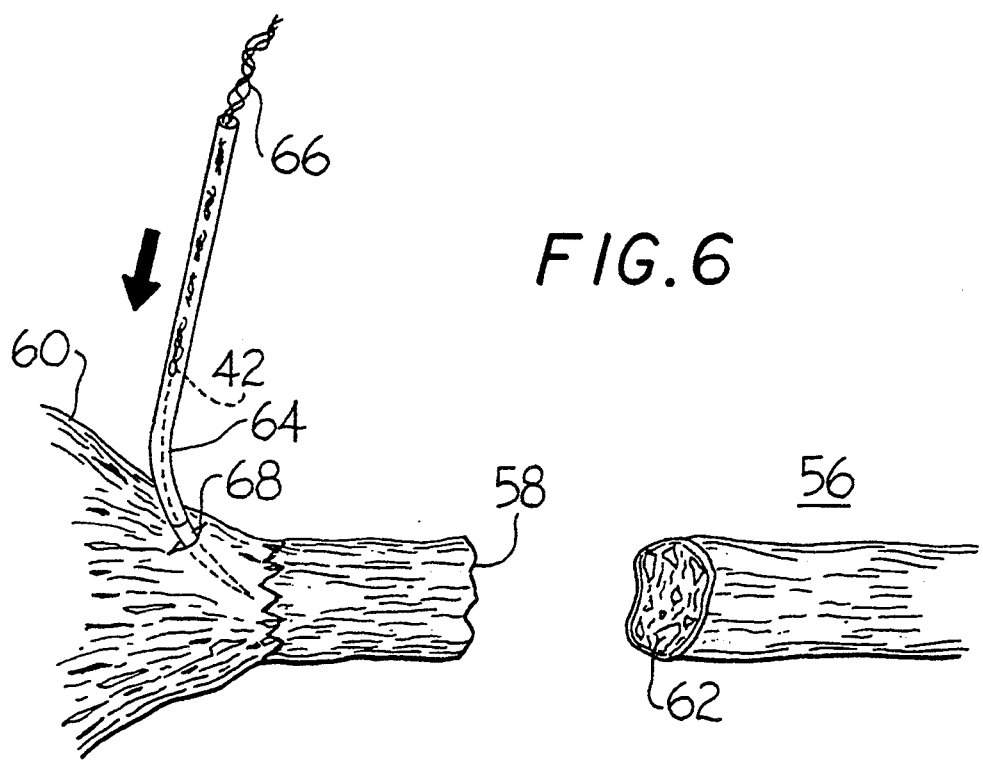
Figure 7:
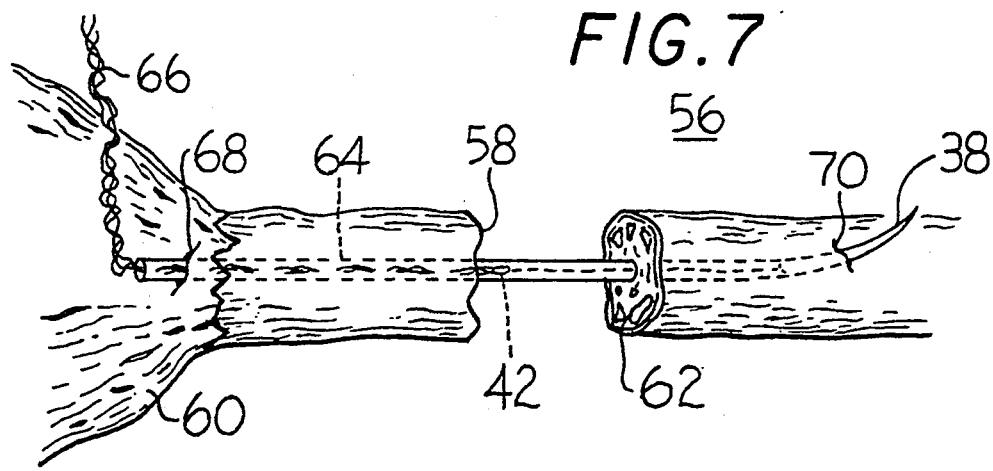
Figure 8:
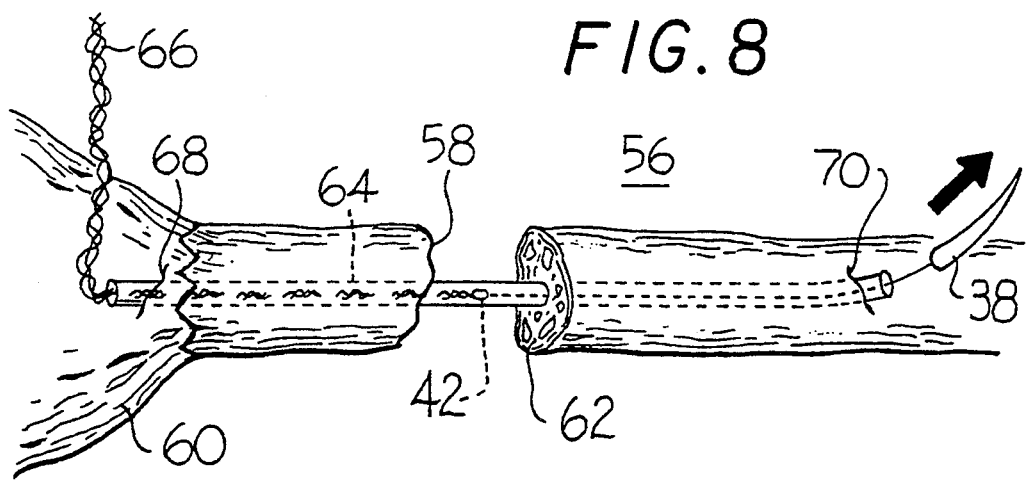
Figure 9:
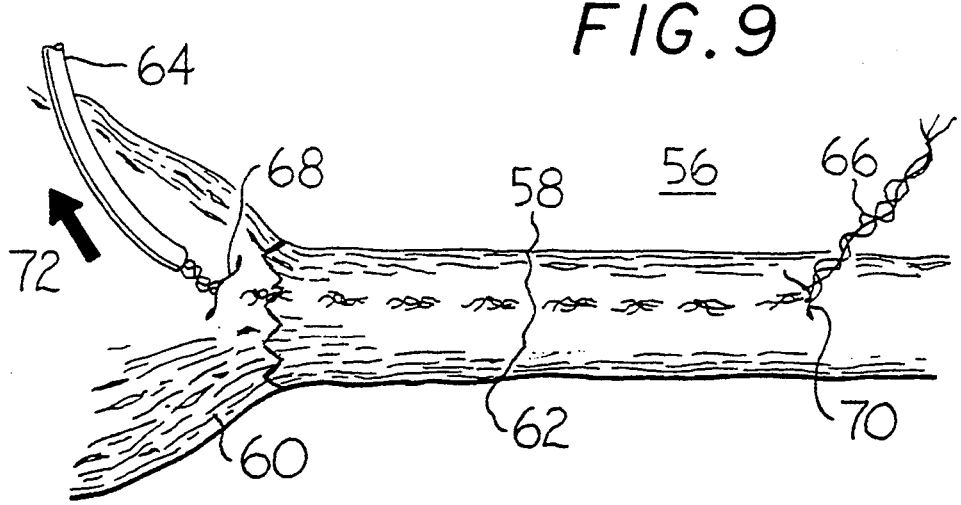

Referring now to FIGS. 6-7, implant assist apparatus 64, as shown disassembled in FIG. 3, is used to implant the braided stay suture 66 starting at the muscle tissue 60, through first and second ends, 58 and 62, respectively, to emerge from tendon 56 remote from second end 62.

Prior to initiating the repair procedure using this embodiment of the present invention, the implant assist apparatus is prepared by removing arcuate point 38 from cannula 36 such that wire 40 and wire loop 42 are exposed. A suitable length of suture appropriate for the procedure is selected. Typically, a length is selected such that when the suture is doubled over, about six inches of suture are exposed on each end of cannula 36. One end of the suture 66 is threaded through loop 42 and pulled until approximately equal lengths of the suture are disposed on either side of the loop 42. Both ends are threaded into proximal end 41 until the suture ends exit the distal end 44 of cannula 36. The suture 66 is then pulled until loop 42 enters the cannula 36 and arcuate point 38 seats in the proximal end 41 of cannula 36.

The implant assist apparatus 64 is now ready to be passed into tissue across the site which is being repaired. Point 38 is inserted into muscle tissue 60 at location 68 remote from first tendon end 58. The apparatus 64 is guided through the tissue, passing through both first and second tendon ends, 58 and 62 respectively, until point 38 emerges from the tendon at exit site 70. At this stage, distal end 44 of cannula 36 should be exposed at entry location 68 and point 38 should extend out of exit location 70 a distance sufficient to expose proximal end 41 of cannula 36. See FIG. 7.

While holding cannula 36 near the exposed distal end 44, point 38 is detached until loop 42 containing suture 66 is visible. Suture 66 is then pulled carefully until approximately equal lengths are exposed from proximal and distal ends of cannula 36. By gripping one end of suture 66 (in this case the end extending from exit location 70) cannula 36 is pulled out of entry location 68 in the direction of arrow 72 leaving the suture 66 in position. See FIG. 9.

Figure 10:
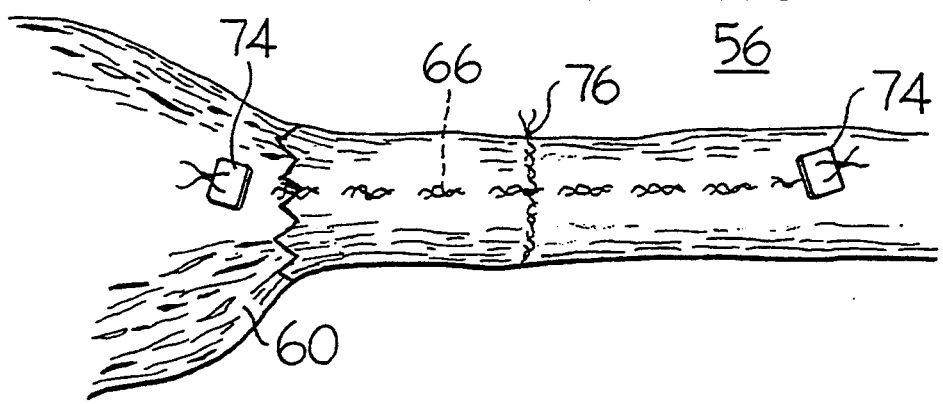

The ends of suture 66 are then tied off, preferably using oblong tying buttons 74 as shown in FIG. 10, to close the ends of the tendon defect to promote healing. Where desired, whipping sutures 76 may be used to close any unsatisfied ends of the tendon 56. Also, surgical needles may be attached to the free ends of the exposed suture and additional suturing and tying may be performed to fully anchor the suture and complete the repair.

To the extent not already indicated, it also will be understood by those of ordinary skill in the art that any one of the various specific embodiments herein described and illustrated may be further modified to incorporate features shown in other of the specific embodiments.

The invention in its broader aspects therefore is not limited to the specific embodiments herein shown and described but departures may be made therefrom within the scope of the accompanying claims without departing from the principles of the invention and without sacrificing its chief advantages.

What is claimed is:

1. An implant assist apparatus for implanting material in tissue to be approximated or reinforced comprising:
    cannula means having a hollow body and an open proximal and distal end;
    point means detachably fixed to said open proximal end of the cannula means for penetrating tissue;
    guide wire means attached to said point means and extending into said open proximal end of the cannula means; and
    implant material releasably attached to said guide wire means and extending from said open distal end of the cannula means.

2. An implant assist apparatus as in claim 1 further comprising a loop formed in the end of said guide wire means extending into the cannula.

3. An implant assist apparatus as in claim 1 wherein said cannula means is linear in shape.

4. An implant assist apparatus as in claim 1 wherein said cannula means is arcuate in shape.

5. An implant assist apparatus as in claim 1 wherein said cannula means is partially linear and partially arcuate in shape.

6. An implant assist apparatus as in claim 1 wherein said cannula means further comprises at least one flute formed longitudinally therein.

7. An implant assist apparatus as in claim 1 wherein said point means is formed in the shape of a trocar.

8. An implant assist apparatus as in claim 1 wherein said point means is formed in the shape of an arcuate cone.

9. An implant assist apparatus as in claim 1 wherein said point means is formed integrally with said cannula means and is detachable therefrom.

10. An implant assist device as in claim 1 wherein said implant material is selected from the group consisting of sutures, prosthetic devices and tissue augmentation devices.

11. An implant assist apparatus as in claim 1 wherein said implant material comprises a braided suture.

12. An implant assist apparatus as in claim 2 wherein said loop remains within said cannula means when said point means is in position.

13. A method of implanting material in tissue for reapproximating or reinforcing defects therein comprising the steps of:
    providing cannula means having a hollow body open at both ends and a detachable point at a proximal end thereof, said detachable point having a guide wire attached and extending into said hollow body;
    attaching a length of implant material to said guide wire;
    passing said cannula means with detachable point and implant material into the tissue at an entry point remote from one side of the defect and out of an exit point in an opposite side remote from the defect such that a distal end of said hollow body extends from the entry point and a distal end extends from said exit point;
    removing said detachable point from said cannula means and drawing the guide wire with implant material attached out of the proximal end of said hollow body until the implant material is exposed at both the distal and proximal ends of the hollow body, withdrawing said cannula means from said tissue, leaving the implant material in place, and anchoring the implant material to reapproximate or reinforce the defect.

14. A method of implanting material as in claim 13 wherein said length of implant material is at least partially contained within said hollow body.

15. An implant assist apparatus for implanting material in tissue to be reapproximated or reinforced comprising:

a rigid cannula having an elongate hollow body, an open proximal end, and an open distal end; and a point detachably fixed to said open proximal end of the cannula for penetrating tissue.

16. An implant assist apparatus as in claim 15 further comprising longitudinal flutes formed in the body of the cannula.

17. An implant assist apparatus as in claim 15 further comprising an implant material preattached through said cannula to said point.

18. An implant assist apparatus as in claim 17 wherein said implant material comprises at least one suture.

19. An implant assist apparatus as in claim 18 wherein said implant material comprises at least one braided suture.

20. An implant assist apparatus as in claim 15 wherein said point is formed in a shape selected from the group consisting of trocar, conical, convex, arcuate conical, tapered, reverse cutting, side cutting, and flattened conical.

21. An implant assist apparatus as in claim 20 wherein said point is dimensioned to have substantially the same diameter as said cannula.

22. An implant assist apparatus as in claim 15 wherein said cannula is substantially circular in cross-section.

23. An implant assist apparatus as in claim 15 wherein said cannula is formed in a shape selected from the group consisting of linear, arcuate and partially arcuate.

24. A surgical implant assist apparatus for implanting suture material in tissue comprising:

a rigid tubular cannula having a hollow body and first and second ends;

a point removably attached to said first end of said tubular cannula for penetrating tissue; and at least one surgical suture positioned at least partially in the tubular cannula.

25. A surgical implant assist apparatus as in claim 24 wherein said at least one surgical suture is a braided suture.

26. A surgical implant assist apparatus as in claim 24 further comprising flutes formed in at least a portion of said tubular cannula.

27. A surgical implant assist apparatus as in claim 24 wherein said point is formed in a shape selected from the group consisting of trocar, conical, concave, convex, arcuate conical, tapered, reverse cutting, side cutting and flattened conical.

28. A surgical implant assist apparatus as in claim 24 wherein said tubular cannula is formed in a shape selected from the group consisting of linear, arcuate and partially arcuate.

29. A surgical implant assist apparatus as in claim 24 wherein said point is integrally formed with said tubular cannula and is detachable therefrom.

* * * * *